United States Patent [19]

Murdock et al.

[11] Patent Number: 4,696,935

[45] Date of Patent: Sep. 29, 1987

[54] METHOD OF TREATING TRANSPLANTED TUMORS AND MODULATING THE IMMUNE RESPONSE

[75] Inventors: Keith C. Murdock, Pearl River, N.Y.; Martin R. Damiani, Allendale; Frederick E. Durr, Ridgewood, both of N.J.

[73] Assignee: American Cyanamid Company, Stamford, Conn.

[21] Appl. No.: 315,559

[22] Filed: Oct. 27, 1981

Related U.S. Application Data

[60] Division of Ser. No. 183,612, Sep. 2, 1980, Pat. No. 4,314,061, which is a continuation-in-part of Ser. No. 89,805, Oct. 31, 1979, abandoned, which is a continuation-in-part of Ser. No. 954,279, Oct. 24, 1978, abandoned, which is a continuation-in-part of Ser. No. 821,039, Aug. 1, 1977, abandoned.

[51] Int. Cl.$^4$ .............................................. A61K 31/44
[52] U.S. Cl. .................................................... 514/297
[58] Field of Search .................... 424/257, 248.4, 250; 514/297

[56] References Cited

U.S. PATENT DOCUMENTS 1,727,480  9/1929  Mietzsch ............................ 546/104
3,740,403  6/1973  Murdock ............................ 546/103

Primary Examiner—Jerome D. Goldberg
Attorney, Agent, or Firm—Edward A. Conroy, Jr.

[57] ABSTRACT

This disclosure describes compositions of matter useful for inducing the regression of transplanted tumors in warm-blooded animals and for enhancing the immune system, and the method of treatment of transplanted tumors and enhancing the immune response in mammals therewith, the active ingredients of said compositions of matter being 3,6-bis[2-(1-piperidino)ethoxy]acridine or the pharmacologically acceptable acid-addition salts thereof.

3 Claims, No Drawings

METHOD OF TREATING TRANSPLANTED TUMORS AND MODULATING THE IMMUNE RESPONSE

CROSS REFERENCE TO RELATED APPLICATION

This application is a division of our application Ser. No. 183,162, filed Sept. 2, 1980, now U.S. Pat. No. 4,314,061 which is a continuation-in-part of our abandoned application Ser. No. 89,805, filed Oct. 31, 1979 which is a continuation-in-part of our abandoned application Ser. No. 954,279, filed Oct. 24, 1978 which is a continuation-in-part of our abandoned application Ser. No. 821,039, filed Aug. 1, 1977.

BRIEF SUMMARY OF THE INVENTION

This invention is concerned with 3,6-bis[2-(1-piperidino)ethoxy]acridine. This compound forms acid-addition salts with a variety of pharmaceutically acceptable organic and inorganic salt-forming reagents. These acid-addition salts, formed by admixture of the free base with one, two or three equivalents of an acid, suitably in a neutral solvent, are formed with such acids as sulfuric, phosphoric, hydrochloric, hydrobromic, nitric, citric, lactic, tartaric, acetic and related acids. For purposes of the present invention, the free base is equivalent to its non-toxic acid-addition salts.

3,6-bis[2-(1-piperidino)ethoxy]acridine may be prepared by reacting 3,6-acridinediol with 1,2- or 1,3-dihaloalkanes or 1-halo-2, or 3-hydroxysulfonyl alkanes in a solvent such as dimethylformamide for 15 minutes to 2 hours. The resulting bis(haloalkoxy)acridine can then be reacted with piperidine, preferably in a sealed bomb at 80°–150° C., for 10–50 hours. The product may be isolated by removing the inert solvent from the reaction mixture by evaporation, taking up the residue in water and extracting the aqueous phase with diethyl ether. Evaporation of the ether provides the product which may then be purified by advance chromatography.

The 3,6-acridinediol disodium salts may be prepared as described in the literature by treating substituted 3,6-acridinediol with sodium hydride at room temperature in an inert solvent such as dimethylformamide for 15–30 minutes.

DETAILED DESCRIPTION OF THE INVENTION

In recent years, the concept of surgical-adjuvant chemotherapy for the treatment of solid neoplasms has become widely accepted by clinical oncologists. Surgery is an effective treatment modality for the removal of the bulk of a large primary tumor, but often is not applicable to the removal of small, widely scattered metastatic foci of disease. It is recognised that the principal cause of death of cancer patients is the growth of unresolved metastatic tumor foci. Systemic chemotherapy, as an adjunct to surgery, is ideally suited to the elimination of tumor metastases, and has been responsible for much of the progress made in the treatment of human solid tumors.

There are a variety of experimental animal tumor models that are used to assess the therapeutic effects of drugs on primary and metastatic tumor growth. The Lewis lung carcinoma is a highly malignant anaplastic murine carcinoma which when implanted subcutaneously gives rise to a large primary tumor that metastasizes to the lungs in the early stages of tumor growth. Surgical removal of the primary tumor is not curative unless performed within six days of tumor implantation, thereby preventing metastatic spread of tumor to the lungs. The actual cause of death of the experimental animals, even in the continued presence of the primary tumor, is the growth of the metastatic lung tumors. In this model system, therapeutic drug activity would be indicated by the inhibition of growth of the primary tumor (thereby preventing metastasis formation), or in conjunction with non-curative surgical removal of the primary tumor, by inhibiting the growth of lung metastases. This would be indicated by an increase of median survival time and an increase in the number of long term survivors (i.e. "cures") among drug treated mice when compared to mice that had received non-curative surgery and placebo instead of drug. Alternatively, the Lewis lung carcinoma can be implemented intravenously in mice to establish "artificial" metastases in the lungs. Therapeutic drug activity, in this instance, would be reflected by an inhibition of the growth of these lung tumor metastases.

The B16 melanoma implanted subcutaneously in mice gives rise to a large primary tumor which metastasizes to many distant sites. Surgery is curative when carried out early during the growth of the primary tumor, before metastatic spread of the tumor has occured. Systemic chemotherapy in conjunction with non-curative surgery, has been demonstrated to prevent metastatic tumor spread or to inhibit the growth of metastases formed prior to surgical removal of the primary tumor. Effective chemotherapy, in the latter instance, is indicated by an increased median survival time or an increased number of long term survivors (i.e. "cures") among drug treated mice when compared to placebo treated mice.

The active compound of the present invention is active when tested according to the following procedures:

(A) Antitumor Activity Against Intravenously Inoculated Lewis Lung Carcinoma in Mice Lewis lung carcinoma cells, $5 \times 10^5$ viable cells, are injected intravenously into $BDF_1$ mice. The drug was prepared in normal saline and administered once daily, by the oral route, at doses ranging from 38 mg/kg to 400 mg/kg on days 1, 7, and 13 following tumor cell inoculation. A control group of mice received a saline placebo, instead of drug, by the oral route on the same days of treatment. All mice were sacrificed on day 19 following tumor inoculation, their lungs removed and individually weighed. Additionally, a group of 10 normal, non-tumor bearing $BDF_1$ mice, of the same sex, age, and body weight as the tumor bearing mice, were sacrificed and their lungs removed and weighed to determine the average normal lung weight. The average normal lung weight was subtracted from the weight of lungs from the tumored mice to determine the weight of tumorous tissue present in the lungs of the tumor bearing mice. A positive drug effect is indicated by a $\geq 58\%$ reduction in the average lung tumor weight of the drug treated mice, relative to the average lung tumor weight of the saline placebo treated mice.

Reference to this animal model test system is:
(1) "Growth Characteristics and Chemotherapeutic Response of Intravenously Implanted Lewis Lung Carcinoma". Ovejera et al., Cancer Chemotherapy Reports Part 2, vol. 5:111–125, 1975.

(B) Surgical-Adjuvant Antitumor Activity Against Lewis Lung Carcinoma Implanted Subcutaneously in Mice $BDF_1$ mice were inoculated subcutaneously in the right hind footpad with $5 \times 10^5$ viable Lewis lung carcinoma cells, on day zero. The drug was prepared in normal saline and administered by the oral route once daily, on days 1, 7 and 13 following tumor inoculation, at doses ranging from 50 mg/kg to 400 mg/kg. A control group of mice received a saline placebo instead of drug, and another group of tumor bearing mice received the positive control drug cyclophosphamide, at 100 mg/kg, administered by intraperitoneal injection. On the 11th day after tumor implantation, the mice were anesthesized with Nembutal, and the tumor bearing feet surgically amputated above the ankle joint. The surgical incision was swabed with alcohol and sealed with stainless steel would clips. The tumor bearing feet were individually weighed and the average weight of a normal foot (determined by weighing amputated feet from non-tumor bearing mice of the same age, sex, and body weight) was subtracted to obtain the weight of tumor tissue in the amputated foot. Mice were then observed for deaths until the 90th day after tumor implantation. A therapeutic drug effect is indicated by; (a) a significant ($\geq 58\%$) inhibition of growth in the primary footpad tumor, (b) a significant ($\geq 25\%$) increase in life-span of drug treated mice, or (c) a statistically significant ($p < 0.05$) increase in the number of survivors at 90 days; i.e. "cures", relative to the placebo treated control group of mice.

References to this animal model test system are:
(1) "Success and Failure in the Treatment of Solid tumors. Cure of Metaststic Lewis Lung Carcinoma with Methyl-CCNU (NSC-95441) and Surgery-Chemotherapy". Mayo et al., Cancer Chemotherapy Reports 56:183–195, 1972.
(2) "Effectiveness of Clinically Active Antineoplastic Drugs in a Surgical-Adjuvant Chemotherapy Treatment Regimen Using the Lewis Lung (LL) Carcinoma". Merker et al., International Journal of Cancer 21:482–489, 1978.

(C) Surgical-Adjuvant Antitumor Activity Against B16 Melanoma Implanted Subcutaneously in Mice $BDF_1$ mice were inoculated subcutaneously in the right hind footpad with $5 \times 10^5$ viable B16 melanoma cells, on day zero. The drug was prepared in normal saline and administered by the oral route once daily, on days 1, 7, and 13 following tumor implantation, at doses ranging from 50 mg/kg to 400 mg/kg. A control group of mice received a saline placebo instead of drug, and another group of tumor bearing mice received the positive control drug cyclophosphamide, at 100 mg/kg, by intraperitoneal injection. On the 21st day after tumor implantation, the mice were anesthesized with Nembutal, and the tumor bearing feet were surgically amputated above the ankle joint. The surgical incision was swabed with alcohol and sealed with stainless steel wound clips. The tumor bearing feet were individually weighed and the average weight of a normal foot (determined by weighing amputated feet from non-tumor bearing mice of the same sex, age, and body weight) was subtracted to obtain the weight of tumor tissue in the amputated feet. Mice were then observed for deaths unitl the 90th day after tumor implantation. A therapeutic drug effect is indicated by: (a) a significant ($\geq 58\%$) inhibition of growth in the primary footpad tumor, (b) a significant ($\geq 25\%$) increase in the life-span of drug treated mice, or (c) a significant ($p < 0.05$) increase in the number of survivors at +90 days, i.e. "cures", relative to the placebo treated control group of mice.

Reference to this animal model test system is:
(1) "The Potential for Murine Tumor Models in Surgical Adjuvant Chemotherapy". Griswold, D. P. Jr., Cancer Chemotherapy Reports Part 2 vol. 5:187–204, 1975.

(D) Potentiation of Cyclophosphamide Activity Against B-16 LMelanoma in Mice $BDF_1$ male mice are inoculated subcutaneously with 0.25 ml. of a 10% B-16 melanoma homogenate. Cyclophosphamide is administered intraperitoneally at 80 mg./kg. the second day following the day of tumor implantation. Test compounds are given intraperitoneally on days +6, +8 and +10 relative to tumor implantation. Tumors are measured on day +26 with a positive response being indicated by a $\leq 50\%$ inhibition of tumor size compared to the Cytoxan control.

The use of immunomodulants and chemotherapeutic adjuvants constitutes a new therapeutic approach to the treatment of immune deficiencies and cancer and is based on the concept that there are distinctive antigens in or on most tumor cells, such as viral particles and bacteria, that distinguish them from normal host cells, or a particular component of the immune system that can be retulated. A majority of tumor immunologists favor the view that potentially malignant cells constantly arise but because of their "foreigness" they are normally eliminated by a competent humoral and cellular immune system. Occasionally, however, tumor cells escape this immune surveillance and continue to reproduce and cancer results. The reason for the failure of the normally efficient immune surveillance mechanisms are not fully understood but it is thought that the immune system becomes less effective with increasing age. It is depressed in certain genetic immuno-deficiency diseases, in various bacterial, fungal or viral infections, and in patients undergoing immuno-suppressive therapy. The growth of the neoplasm itself, as well as the various therapeutic modalities designed to treat the disease, e.g., cytotoxic chemotherapy and viraliation, leads to a still greater depression of host resistance and results in an increased susceptibility to both exogenous and indogenous infections and perhaps accounts for the reinitiation of tumor growth and metastasis which frequently follows treatment-induced tumor remission.

If depression of the immune system facilitates the growth of malignancies, regulation of any particular facet of immune responses may help the host to overcome residual cancer cells. Therefore, it is considered desirable to search for chemical agents (i.e., immunoregulants) capable of restoring and stimulating the host's own immune defense mechanisms in order to overcome the deficiencies which account for the increased susceptibility to disease and failure to eradicate the cancer. It is acknowledged that such immunoregulating agents would very likely be incapable of arresting the growth of a large rapidly proliferating tumor but that their clinical utility would derive from their capacity to enhance normal immune surveillance mechanisms in patients whose tumor burden has largely been reduced by conventional surgical, radiotherapeutic or chemotherapeutic methods. It would be hoped that the few producing a higher incidence of long term survivors or complete cures.

Experimental studies in animals have demonstrated the antitumor potential of a number of immunoregulants including live organisms of bacillus Calmett-Guerin (BCG), heat-killed cells of *Corynebacterium parvum*, polynucleotides, and the anthelmintic drug, levamisole. Those substances have been shown to stimulate cellular immunity and to produce tumor regressions. Some successes have been claimed in early clinical trials with BCG against malignant melanoma and acute leukemia and with levamisole against lung cancer and breast cancer. Although the antitumor effects produced by these agents have been promising, significant therapeutic benefits have yet to be realized. Since this is a very new therapeutic approach, new drugs and methods of treatment must receive careful clinical evaluation in order to reveal the full potential of these drugs.

Modern research is directed to the discovery of a drug similar to, but more potent than, the known immunoregulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating immunodepression common to cancer patients. This is accomplished by infecting mice either with a leukemia virus which produces both leukemia and a disease-related immunodepression or with a transplantable mammary tumor. Effective drugs are recognized by their ability to restore or enhance the antibody response in the experimental mice.

The active compounds and novel compositions of the present invention are active as immunomodulators when tested according to the following procedures:

(E) Rauscher leukemia virus

Rauscher leukemia virus is inoculated intraperitoneally into BALB/C mice. The virus inoculum is a 20%(W/V) spleen extract made from 21-day infected spleens of BALB/C mice. All mice are within a three gram weight range, with a minimum weight of 18 g., and all mice are of the same sex, usually male. Sheep red blood cells are injected intraperitoneally on the seventh day. There are 5 mice per test group. The test compound is administered orally on the sixth day as 0.5 ml. (in 0.2% Noble agar in saline) at a dose of 37.5 to 600 mg/kg of body weight, and again on the seventh and eighth day, in the same manner. On the fourteenth day the mice are weighed and bled from the retroorbital sinus. The blood is pooled and the harvested serum is stored at 4° C., for 24 hours. Hemagglutinin tests are performed by standard procedures using the microtiter plate technique. Acceptable hemagglutinin titer for leukemic (immunosuppressed) mice is ≦1:128. Positive control compounds are Poly I:C (polyinosinic acid:-polycytidylic acid) administered intraperitoneally on days +6, +7 and +8. Acceptable positive control hemagglutinin titers are 4-fold higher than the titers obtained in leukemic control mice. The results of this test on typical compounds of this invention appear in Tables I and II.

TABLE I

| | Rauscher Leukemia Virus % Reduction in Spleen Size |
|---|---|
| DRUG | % Reduction (mg/kg) |
| 3,6-bis(3-piperidinopropoxy)-acridine trihydrochloride | 74 (50) |
| 3,6-bis(2-piperidinoethoxy)-acridine trihydrochloride | 84 (100) |

TABLE II

| | Antibody Restoration in Mice With Rauscher Virus-Induced Leukemia | | |
|---|---|---|---|
| DRUG | DOSE (mg/kg) | ROUTE | SERUM HEMAGGLUTININ TITER/SALINE CONTROL TITER |
| Poly I:C | 10 | IP | 1024/32 |
| Uninfected Controls | — | — | 2048 |
| 3,6-bis(3-piperidinopropoxy)acridine.3HCl | 50 | ORAL | 1024/32 |
| 3,6-bis(2-piperidinoethoxy)acridine.3HCl | 100 | ORAL | 256/16 |

(F) Interferon Induction

Taconic Farms male white mice, weighing 18–24 grams, are treated by gavage 18 hours before infection with the test compound suspended or dissolved in 1.0 ml. of 0.2% aqueous agar solution. The mice are then infected by subcutaneous injection with one $LD_{95}$ of Columbia SK virus in a 0.2 ml. volume of distilled water. Groups of infected, untreated mice are used as controls to show the lethality of the infection. The test duration is seven days. Serum from surviving animals is collected and used to assay for interferon.

The requisite number of monolayers of L-929 mouse cells in 60×15 mm. tissue culture dishes is prepared. The growth medium is minimum essential medium plus 10% fetal calf serum. Two fold dilutions of the serum starting at 1:10 are made using minimum essential medium plus 2% fetal calf serum as a maintenance medium diluent. A 5 ml. portion of each dilution is added to each of three monolayer sutures and they are incubated at 37° C. overnight. The monolayers are washed twice with warmed minimum essential medium and then challenged with approximately 60 plaque-forming units/dish of vesicular stomatitis value in 0.5 ml. of minimum essential medium. The virus is adsorbed for 60 minutes at 37° C., tilting the dish every 15 minutes to spread the virus and to prevent the monolayers from drying. Following adsorption, each dish is overlayed with 8 ml. of agar medium composed of one part 4% Noble agar containing 0.8 ml./kl. diethylaminoethyl dextran to seven parts minimum essential medium plus 2% fetal calf serum. The agar is allowed to harden and is than incubated at 37° C. The plaque development is observed and stained with 0.1% crystal violet in 20% ethanol at the appropriate time (2-4 days). The number of plaques/dish are counted, the average is calculated and the results are plotted on a curve versus dilution. A compound is considered active at a given dilution if it inhibits 50% or more of the plaque formation, the inhibition being due to the presence of interferon.

Protection of mice against lethal virus infection by oral pre-treatment

Groups of 20 random-bred Swiss male mice were administered a single oral dose of drug at 400 mg/kg, tilorone hydrochloride at 200 mg/kg, or a saline placebo. At 24, 48, 72 and 96 hours after drug treatment, separate groups of mice were injected SC with and $LD_{95}$ dose of the inteferon sensitive virus, Columbia SK. Mice were observed for a period of 14 days post-virus infection to determine if drug pre-treatment produced a significant increase in survival relative to the survival of placebo-treated control mice. Typically, protection from lethal infection with Columbia SK virus is associated with induction of interferon. The results appear in Table III.

TABLE III

| | Antiviral Effect of Drugs Against an Interferon - Sensitive Virus, Columbia SK | | |
|---|---|---|---|
| DRUG | DOSE (mg/kg) | ROUTE | SURVIVORS/TOTAL 14 Days Post Injection |
| 3,6-bis(3-piperi-dinopropoxy)acri-dine.3HCl | 400 | Oral | 12/15 |
| 3,6-bis(2-piperi-dinoethoxy)acri-dine.3HCl | 400 | Oral | 12/15 |
| Poly I:C | — | — | 6/45 |

(G) Stimulation of NK-cell Activity in Normal Mice

The existence of natural killer lyphocytes (NK cells has recently been described in mice, rats and humans. NK cells derived from normal animals and humans mediate the rapid destruction of a wide variety of syngeneic and allogeneic tumor cells and virus infected cells, when tested in vitro. No prior exposure of the animal to tumor cells or viruses is required for NK cell-mediated target cell destruction. The resistance to growth of transplanted tumors in mice has been correlated with high levels of NK cell activity. The rapid rise in the level of NK cell activity in animals following infection with a variety of viruses, bacteria, or transplanted tumor cells suggests a possible role of NK cells in immune surveilance. It has recently been reported that administration of interferon induces or interferon causes a paid and substantial rise in the level of NK cell activity in mice.

References to this stimulation of NK cell activity are:
(1) J. Y. Djeu, J. A. Heinbaugh, H. T. Holden and R. B. Herberman, J. Immunology, 122, 174 (1979).
(2) S. Einhorn, H. Glomgren and H. Grander, Int. J. Cancer, 22, 405–412 (1978).
(3) Authors unknown, Nature, 273, 759, (1978).
(4) Authors unknown, Nature, 277, 221, (1979).

Test Procedure

Groups of 5–10 mice are administered test compounds or a placebo by oral, intraperitoneal, intravenous or subcutaneous routes. Approximately 18 hours later the mice are sacrificed and the spleens from each group of mice removed and pooled by groups. The pooled spleens ae placed in 4° C. serum-free Eagle's minimum essential medium (MEM) and disrupted by gentle homogenation. The resulting single cell suspension is filtered through a 60 mesh nylon screen to remove debris and the cells are collected by centrifugation. The cell pellet is resuspended in 10 ml. of hypotonic phosphate buffered saline (0.0.M sodium chloride +0.001M potassium phosphate buffer, pH 7.0 ) for 5–10 seconds to lyse erythrocytes. A 40 ml. portion of MEM supplemented with 10% fetal calf serum (MCM+F) is added and the cell suspension is filtered to remove aggregated debris. Spleen cells are collected by centrifugation, resuspended in MEM+F and the cell density adjusted to $1-2\times 10^7$ spleen cells per ml. of medium.

Human or murine tumor cells are used as targets of NK cells mediated cytolysis. Target cells are incubated in 0.5 ml of MEM+F containing 50-100u Ci of $^{51}$chromium (as sodium $^{51}$chromate). After incubation at 37° C. for 1–3 hours, target cells are washed with three 40 ml. volumes of cold MEM+F, to remove intracellular $^{51}$chromium. $^{51}$Chromium-labelled target cells are resuspended in MEM+F at a cell density of $0.5-1\times 10^5$ per ml. of medium.

Triplicate assays of each cell suspension, derived from pooled spleens of test compound of placebo treated mice, are prepared to assess NK-cell activity. Spleen cells $(5\times 10^6)$ and $^{51}$chromium-labelled target cells $(1\times 10^5)$ are placed in plastic $10\times 75$ mm. Falcon tubes containing 1.0 ml. of MEM+F. The tubes are incubated at 37° C. for 4 hours, then chilled to 4° C. and centrifuged. Aliquots of cell-free supernatant medium are removed from each assay tube and the quantity of $^{51}$chromium released from lysed target cells is determined. A statistically significant increase in the quantity of $^{51}$chromium released in assays of spleen cells derived from drug treated mice, as compared to assays of spleen cells from placebo treated mice, indicates drug stimulation of NK cell activity.

(H) Lack of Effect on Normal Mouse Bone Marrow

The effect of drugs on normal mouse bone marrow is evaluated by determining total cell counts of femurs and by the ability of surviving cells to form colonies in semi-solid medium. The test compound is administered orally and the reference drug Cytoxan is administered intraperitoneally to $C_{57}BL_6$ male mice. One femur from each of three mice per dose level is assayed 24 hours after treatment. Counts of nucleated cells are performed on pooled marrow suspensions and the clonogenic assay is performed by plating 50,000 cells in one ml. of culture medium in each of four culture dishes. The medium to support bone marrow progenitor cell growth is McCoy's medium supplemented with 0.9% methocel, 1.8% human serum albumin, 10% bovine fetal serum and 10% "conditioned" L-cell medium. Cultures are incubated at 37° C. in a humidified atmosphere and baloneys are counted at seven days.

The compounds of the present invention are effective as immunomodulators (that is, they modulate the immune response) when administered orally in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A practical advantage of this invention is that the active compound may be administered in any convenient manner such as the oral or buccal routes or it may be incorporated directly in the diet.

The compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.5% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweettening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The invention will be described in greater detail in conjunction with the following specific examples.

EXAMPLE 1

3,6-bis(2-chloroethoxy)acridine hydrochloride

To a mixture of 2,36 g. of a 61.14% dispension of sodium hydride in oil and 5.20 g. of 3,6-acridinediol sulfate (2.1 is added) and 50 ml. of N,N-dimethylformamide. After stirring at room temperature for 40 minutes, 6.35 g (4.57 ml.) of chloroethyl methanesulfonate are added to the reaction mixture. The mixture is then stirred at room temperature for 2 hours, then at 50° C. for 2.5 hours, poured into 250 ml. of ice-water and placed in a freezer overnight. The resulting yellow crystals are collected and dissolved in 100 ml. of chloroform. To this solution is added 6 ml. of 6N hydrochloric acid in isopropanol. Dilution of the chloroform solution with ether gives 2.8 g. of the desired product as yellow crystals, m.p. 228°–220° C.

EXAMPLE 2

3,6-Bis(3-chloropropoxy)acridine hydrochloride

To a mixture of 11.80 g. of sodium hydride (61.14% oil dispersion) and 26.0 g. of 3,6-acridinediol sulfate (2:1) is added 250 ml. of dry N,N-dimethylformamide. The mixture is stirred at room temperature for 1.5 hours, then 49.8 g. of 3-chloropropyl-p-toluene sulfonate are added. This mixture is stirred at room temperature for 3 hours and 20 minutes, then at 50° C. for 2 hours. The volatile materials are removed under reduced pressure at 35°–40° C. and the residue is quenched with 1200 ml. of ice-cold saturated aqueous sodium bicarbonate solution. The resulting tan crystals are collected and dissolved in 500 ml. of chloroform. A 30 ml. portion of 6N hydrochloric acid in isopropanol is added and the mixture is diluted with ether. The solid is collected and recrystallized from ether, giving the desired product as tan crystals, m.p. 211°–213° C.

EXAMPLE 3

3,6-bis[3-(1-piperidino)propoxy]acridine

The compound is prepared from 3,6-bis(3-chloropropoxy)acridine hydrochloride and piperidine by heating in a steel bomb at 100° C. for 24 hours and the free base is isolated.

EXAMPLE 4

3,6-bis[3-(1-piperidino)propoxy]acridine trihydrochloride

The trihydrochloride salt of 3,6-bis[3-(1-piperidino)propoxy]acridine is prepared by dissolving the free base in 50 ml. of ethanol and 10 ml. of 6N hydrochloric acid in isopropanol, heating to boiling, adding water until a clear solution is obtained and cooling.

We claim:

1. A method of stimulating the immune response in a mammal in need of such stimulation which comprises administering to said mammal an effective immunostimulating amount of a compound selected from the group consisting of 3,6-bis[2-(1-piperidino)ethoxy]acridine and the pharmacologically acceptable acid-addition salts thereof.

2. The method according to claim 1 wherein the compound is 3,6-bis[2-(1-piperidino)ethoxy]acridine free base.

3. The method according to claim 1 wherein the compound is 3,6-bis[2-(1-piperidino)ethoxy]acridine trihydrochloride.

* * * * *